(12) United States Patent
Schmidt

(10) Patent No.: US 7,939,804 B2
(45) Date of Patent: May 10, 2011

(54) SYSTEM AND METHOD FOR DETECTING GAS LEAKS

(75) Inventor: Roger Schmidt, Shorewood, MN (US)

(73) Assignee: Fluke Corporation, Everett, WA (US)

( * ) Notice: Subject to any disclaimer, the term of this patent is extended or adjusted under 35 U.S.C. 154(b) by 195 days.

(21) Appl. No.: 12/324,649

(22) Filed: Nov. 26, 2008

(65) Prior Publication Data

US 2010/0127173 A1 May 27, 2010

(51) Int. Cl.
*G01N 21/00* (2006.01)
(52) U.S. Cl. .................................................. 250/338.5
(58) Field of Classification Search ............... 250/338.5
See application file for complete search history.

(56) References Cited

U.S. PATENT DOCUMENTS

| 3,032,655 | A | * | 5/1962 | Romans | 250/340 |
| 3,925,666 | A | * | 12/1975 | Allan et al. | 250/338.5 |
| 5,430,293 | A | * | 7/1995 | Sato et al. | 250/330 |
| 5,656,813 | A | * | 8/1997 | Moore et al. | 250/330 |

* cited by examiner

*Primary Examiner* — Constantine Hannaher
(74) *Attorney, Agent, or Firm* — Perkins Coie LLP

(57) ABSTRACT

A gas detection system is disclosed that uses an infrared illumination source and an infrared imaging detector. The infrared source is selected to emit at wavelengths corresponding to an absorption band of a gas to be detected. The region to be analyzed for the gas is illuminated, and the infrared radiation reflects off of local surfaces back to the imaging detector. At locations where the gas is present, the infrared radiation is absorbed which reduces the back reflection to the detector.

19 Claims, 4 Drawing Sheets

SYSTEM AND METHOD FOR DETECTING GAS LEAKS

TECHNICAL FIELD

The present disclosure relates to detecting locations of gas leaks by imaging an area illuminated by infrared radiation within an absorption band of the gas to be detected.

BACKGROUND

Thermal imaging cameras are useful for detecting radiation in the infrared wavelength range and for producing images of the infrared radiation. Filters can be used to limit the wavelengths of infrared radiation to which the thermal imaging camera is exposed.

Absorption spectroscopy is a technique that measures the intensity of a beam of radiation before and after the radiation has interacted with an unknown sample of material to be analyzed. The incident photons in the beam of radiation are absorbed at the particular wavelengths that correspond to the available energy levels present in the material in the sample. For example, an elevated temperature blackbody radiation source can be placed behind a sample to be analyzed, and the wavelength bands at which the blackbody radiation is absorbed, particularly in the infrared region, provides information that can be used to identify the sample of material. Thermal imaging cameras can be used to image the sample in this type of application. However, placing an elevated temperature blackbody behind a potential leak is impractical and often the signal levels without it are so low that detecting a potential leak is illusive.

In the past, ultraviolet leakage detectors have been used for detecting gas leaks. A dye, which has the property of fluorescing in the visible range when it is illuminated at a particular wavelength band in the ultraviolet range, is injected into the gas. When the dye-injected gas leaks and is appropriately illuminated with ultraviolet radiation, the dye visibly fluoresces, thus indicating the location of leaks to an observer. One example where the dye-injected gas has been useful is detection of leaks in an air conditioning line.

SUMMARY

The absorption bands of a gas to be detected are determined, and an infrared source emitting at at least one of the wavelengths within the absorption bands is used to illuminate an area to be analyzed. In areas where there is no gas, the infrared illumination reflects off of surrounding surfaces back to an infrared imager. In locations where the gas has leaked, the infrared illumination is absorbed by the gas, thus reducing the amount of infrared illumination reflected back to the infrared imager from that location. By determining the locations where the reflected infrared source has been attenuated, locations of gas leaks can be identified.

BRIEF DESCRIPTION OF THE DRAWINGS

Examples of a gas leak detection system and method are illustrated in the figures. The examples and figures are illustrative rather than limiting.

DETAILED DESCRIPTION

Figure 1:
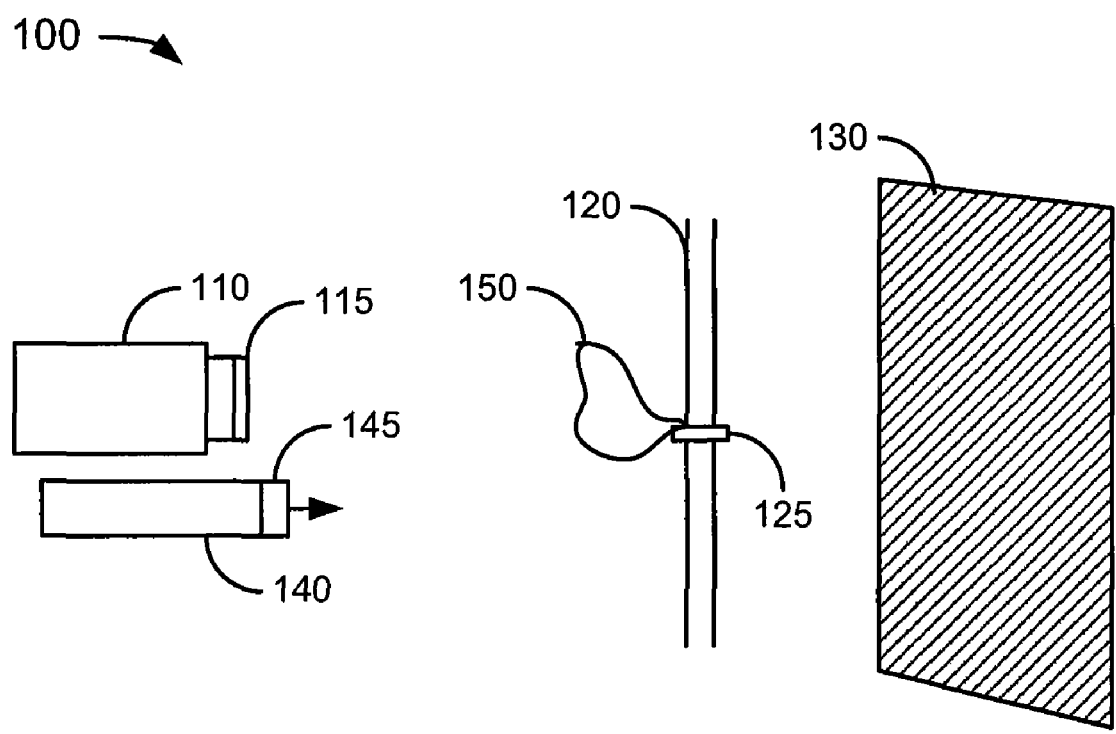
FIG. 1 shows a typical environment in which an infrared camera can be used to detect a gas leak from a pipe.

Described in detail below is a method of detecting gases that may arise from gas leaks. An infrared illumination source is used to illuminate the area to be observed. The wavelength or wavelength band of the illumination source is selected to match an absorption band of the gas to be detected and also an atmospheric transmission window. The infrared illumination reflects off of the surrounding equipment and back to an infrared imaging detector. Any gas that has leaked absorbs the infrared illumination, thus eliminating or reducing the back reflection to the imaging detector and producing a high contrast with other background reflections.

The following description and drawings are illustrative and are not to be construed as limiting. Numerous specific details are described to provide a thorough understanding of the disclosure. However, in certain instances, well-known or conventional details are not described in order to avoid obscuring the description.

Without intent to further limit the scope of the disclosure, examples of instruments, apparatus, methods and their related results according to the embodiments of the present disclosure are given below. Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

The terminology used in the description presented below is intended to be interpreted in its broadest reasonable manner, even though it is being used in conjunction with a detailed description of certain specific examples of the invention. Certain terms may even be emphasized below; however, any terminology intended to be interpreted in any restricted manner will be overtly and specifically defined as such in this Detailed Description section.

There are many applications for which detection of a leaking gas would be useful. For example, leaking gases at an oil refinery may be poisonous, such as hydrogen sulfide, or explosive, such as propane or methane. In other examples, sulfur hexafluoride ($SF_6$), which is used as a gaseous dielectric medium, may leak from high-voltage circuit breakers, switchgear, or other electrical equipment in utility switchyards and damage the equipment; refrigerants, such as chlorofluorocarbons, may leak from refrigeration systems and be harmful to the environment; and natural gas may leak from gas pipelines and storage facilities resulting in significant financial losses.

FIG. 1 shows an example of a typical scenario 100 in which an infrared camera or any other type of infrared detecting element 110 can be used to detect a gas leak 150 from a pipe 120 or any other gas-containing equipment.

In the example of FIG. 1, a portion of a pipe 120 is shown that has a connection 125 from which a gas 150 is leaking. The gas 150 can leak from any type of gas confining equipment including through welds, cracked containers, and broken seals.

An infrared source 140 is used to illuminate a region of interest in which a gas potentially may be leaking with radiation in the infrared spectrum. The infrared spectrum generally covers the range from approximately 700 nm to approximately 1 mm. However, the wavelength or wavelengths at which the infrared source 140 emits illumination should overlap with at least a portion of one absorption band of the gas to be detected. In one embodiment, for a higher signal to noise ratio, the wavelength of the infrared source overlaps the peak absorption wavelength within the absorption band of the gas. In one embodiment, the infrared source 140 can be a laser or a narrowband source. In one embodiment, the infrared source 140 can be a tunable laser or tunable narrowband source that is tunable over at least a portion of the infrared spectrum. Typically, a stronger infrared source such as a laser source will provide a better signal to noise ratio for identifying locations where the gas is present.

When the gas to be detected is present in the atmosphere, the effect of absorption of electromagnetic radiation by the atmosphere should be considered. Gas detection analysis should occur at wavelengths overlapping an atmospheric transmission window because an atmospheric transmission window is one of the wavelength bands in the electromagnetic spectrum at which the earth's atmosphere has minimal absorption. One of these atmospheric transmission windows can be found in the near-infrared range with wavelengths between approximately 3-5 microns and also between approximately 7-14 microns. There are several other atmospheric transmission windows that can also be used.

In one embodiment, infrared optics 145 may be used to shape the infrared radiation emitted by the infrared source 140, for example, converging, diverging, and/or conditioning the radiation, in order to illuminate a specific region of interest. The infrared optics 145 can be coupled to the infrared source 140 or independent of the infrared source 140. In one embodiment, the same infrared optics may be used to focus the reflected infrared radiation onto an infrared imaging element such as an infrared camera 110 if the source 140 and imaging element 110 are in close proximity.

The infrared camera 110 is used to image the infrared radiation generated by the infrared source 140 and reflected from the region of interest. In one embodiment, one or more optical filters 115 are used to attenuate the wavelengths of radiation outside an absorption band of a gas to be detected. One or more optical bandpass filters could be used to attenuate the unwanted wavelengths of radiation. Alternatively or additionally, one or more optical lowpass and highpass filters could be used together to attenuate the wavelengths of radiation outside an absorption band. The infrared camera 110 can be placed in a fixed location to take images of the same scene periodically. In some embodiments, the infrared camera 110 can be used to scan one or more areas periodically.

In one embodiment, the infrared illumination source 140 can be used by one or more infrared imaging detectors 110 in the same local region.

Alternatively, the infrared illumination source 140 can be coupled to the infrared imaging detector 110 and/or integrated into a single instrument so that the gas detection system is portable and easily can be carried by a technician to analyze a potential gas leakage site. For example, when the gas-containing equipment is first installed and during or after maintenance work is performed on the equipment, a technician can set-up the equipment as an early warning gas detection system.

Any gas that has leaked, such as from a confinement container or equipment, will absorb the infrared radiation because the wavelength of the infrared radiation was selected to be within an absorption band of the gas to be detected. Because the presence of the gas absorbs at least some of the infrared illumination, the amount of infrared illumination reflected back to the infrared camera will be reduced or even eliminated at the locations where the gas is present as a result of the leak. In contrast, reflections from the equipment or other surfaces, such as walls and fences, do not absorb the infrared radiation. Typically, there will be a higher concentration of gas in the vicinity of the leak source because the gas can dissipate in the environment as it travels away from the leak source. Thus, there will be stronger absorption of the infrared illumination near the leak source. Consequently, when the infrared camera images the infrared illumination reflected from the region, there will be a high contrast between locations where the gas is densely present and locations where there is no gas or dissipated gas. Moreover, very small gas leaks also can be detected with this method. By combining a strong infrared illumination source with a low cost infrared camera, a high signal to noise ratio can be achieved in identifying locations from where the gas is leaking.

In one embodiment, if the infrared illumination source 140 is wideband such that the infrared illumination covers a number of non-overlapping absorption bands for different gases, different gases can be detected with a single source. The gas leak locations for the different individual gases can be imaged by adjusting the wavelength filter 115 at the infrared camera 110 to transmit only the wavelengths within a single absorption band corresponding to a particular gas.

In one embodiment, a tunable infrared illumination source 140 can be used in conjunction with different wavelength filters 115 at the infrared camera 110. When the illumination source 140 is tuned to a particular absorption band for a specific gas, the wavelength filter 115 is adjusted to transmit wavelengths in that absorption band. In one embodiment, a filter or series of filters can be coupled to the tunable source 140 to attenuate wavelengths outside of the absorption band of a particular gas if the spectrum of the emitted radiation is not sufficiently narrowband to remain within the absorption band of the gas to be detected.

In one embodiment, an infrared reflecting screen 130 can be placed behind the region of interest to reflect the infrared radiation from the infrared source 140 and provide a better contrast for imaging the absorption of infrared radiation by any leaking gas. Environments where the reflecting screen 130 would be useful include, but are not limited to, when the gas leak is outside or when there are very few pieces of equipment or other objects near a potential leak source to reflect the illuminating infrared radiation.

In one embodiment, the infrared reflecting screen 130 can be made of or coated with any aluminized metal. Alternatively, the reflecting screen can be made from any material that reflects infrared radiation at the wavelengths of the absorption band of the gas to be detected.

In one embodiment, the infrared camera 110 can be configured with an alarm to provide an indication of a gas leak. Non-limiting examples of an alarm include, but are not limited to, an audio alarm such as a beep at the infrared camera to alert a serviceman performing the gas leak detection and an audio alarm at a remote location such as at a central office. Thus, when a serviceman uses an infrared camera 110 to conduct routine checks of equipment or gas lines on a regular basis, the alarm will automatically sound when a gas leak is detected.

Figure 2A:
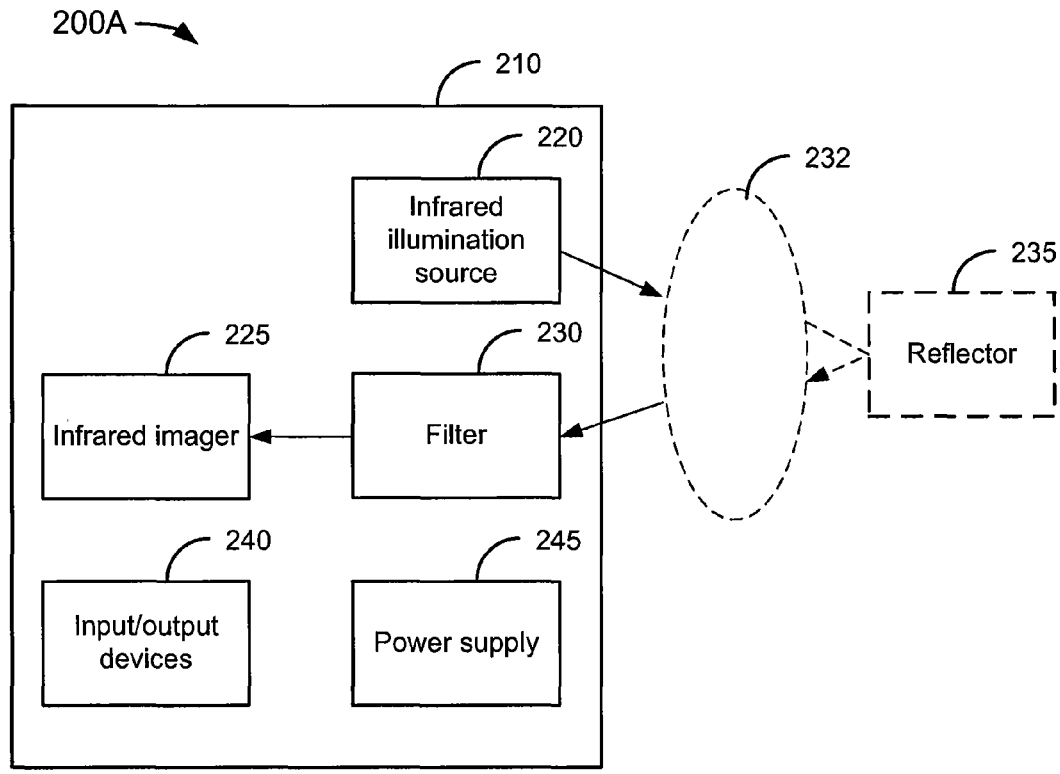
FIG. 2A shows a suitable block diagram of an infrared imaging system, according to an embodiment of the disclosure.

FIG. 2A shows a suitable block diagram of an infrared imaging system 200A, according to an embodiment of the disclosure. The infrared imaging system includes a combination infrared source and imager 210 and an optional external reflector 235 located behind an area 232 where potential gas leaks are to be detected. The combination infrared source and imager 210 includes an infrared illumination source 220, a filter 230, an infrared imager 225, input/output devices 240, and a power supply 245.

The infrared illumination source 220 can be any illumination source that emits infrared illumination, either broadband or narrowband. The emission wavelengths of the infrared source 220 should be selected to include wavelengths that fall within the absorption band or bands of the gas to be detected. The infrared source 220 may use optional infrared optics to shape the emitted infrared radiation.

The infrared imager 225 is used to image any infrared radiation generated by the infrared source 220 and reflected from the region of interest 232. The infrared imager 225 can be an infrared camera. One or more optical filters 230 are used to attenuate wavelengths outside the absorption band or bands of interest of a gas to be detected before the radiation reaches the imager 225. The optical filters 230 may be one or a combination of the following: bandpass filters, low-pass filters, and high-pass filters.

An optional reflector 235 is used help reflect infrared radiation from the infrared source to the infrared camera 225 in order to increase the signal to noise ratio. The reflector may not be necessary if there are sufficient surfaces in the vicinity of the region to be imaged that can reflect infrared radiation.

Input/output devices 240 may include, but are not limited to, triggers to start and stop the infrared imaging system or to initiate other imaging system functions, visual displays, speakers, and communication devices that operate through wired or wireless communications. A power supply 245 may include, but is not limited to, a battery.

Figure 2B:
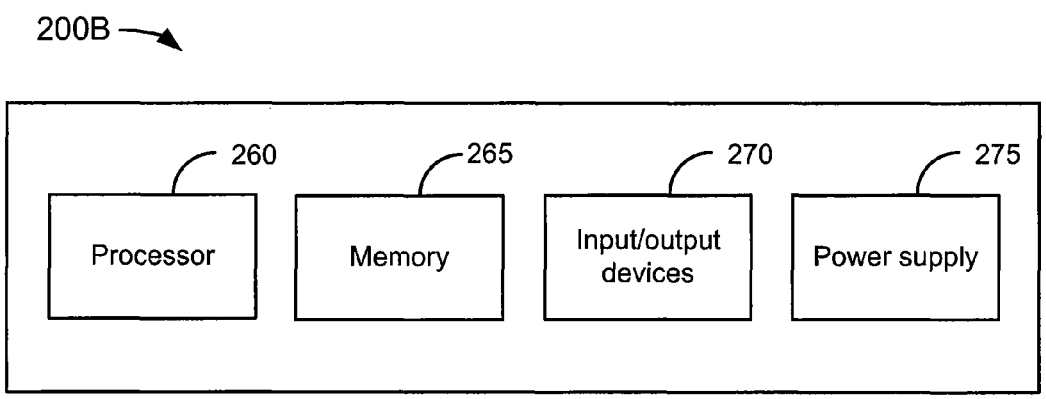
FIG. 2B shows a suitable block diagram of an infrared imaging data processing system, according to an embodiment of the disclosure.

FIG. 2B shows a suitable block diagram of an infrared imaging data processing system 200B, according to an embodiment of the disclosure. The infrared imaging data processing system includes a processor 260, memory 265, input/output devices 270, and a power supply 275.

The processor 260 may be used to run infrared imaging data processing applications. Memory 265 may include, but is not limited to, RAM, ROM, and any combination of volatile and non-volatile memory. The imaging data received from the infrared imaging system 200A can be stored in the memory 265. The processed imaging data can also be stored in the memory 265.

Input/output devices 270 may include, but are not limited to, triggers to start and stop the infrared imaging data processing system or to initiate other data processing functions, visual displays, speakers, and communication devices that operate through wired or wireless communications. The infrared imaging data processing system can receive imaging data from the infrared imaging system 200A. A power supply 275 may include, but is not limited to, a battery. In one embodiment, the infrared imaging data processing system 200B can transmit processed data to another device, server, and/or database.

Figure 3:
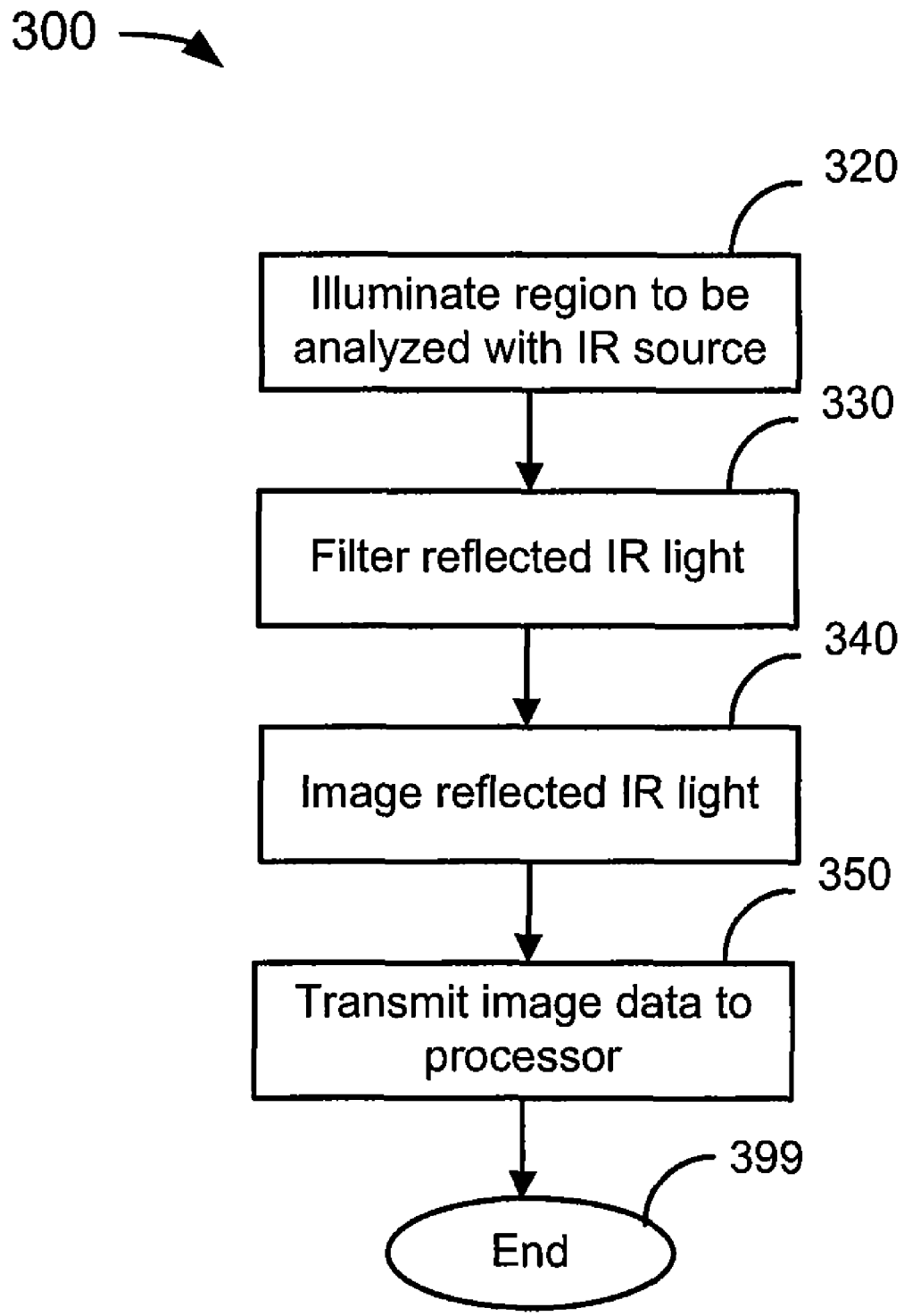
FIG. 3 depicts a flow diagram illustrating an exemplary process for imaging a gas leak, according to an embodiment of the disclosure.

FIG. 3 depicts a flow diagram illustrating an exemplary process 300 for imaging a gas leak, according to an embodiment of the disclosure.

Prior to imaging for a gas leak, the absorption band or bands of a gas to be detected should be determined. Ways in which the information may be determined include looking up the information in scientific literature and performing absorption experiments with the particular gas. Typically, only the absorption bands of the gas to be detected that are within standard atmospheric transmission windows would be useful if the region to be evaluated were in a normal atmospheric environment. However, in a vacuum or otherwise controlled environment, absorption bands of the gas outside standard atmospheric transmission windows may also be useful. Using this information, manufacturers can target imagers intended for detecting certain gases to be sold or packaged with the appropriate infrared source and filter.

At block 320, the region to be analyzed for a gas leak is illuminated with an infrared source. The infrared source can provide continuous illumination or may be pulsed in a particular manner in conjunction with the detection techniques used by the infrared imager 225 such that the signal to noise ratio is enhanced.

At block 330, the infrared radiation reflected from the scene is optically filtered to improve the signal to noise ratio. Filtering is useful if the infrared source used in block 320 is not sufficiently narrowband or sufficiently strong.

At block 340, the reflected infrared radiation is imaged by an infrared camera or other imager. The infrared camera can be mounted in one location to take images of a fixed region. Alternatively, a mounted infrared camera can scan one or more regions of interest to provide better resolution or to cover areas that are so large that the infrared camera cannot image them simultaneously. In one embodiment multiple fixed infrared cameras or imagers are used together to provide a composite image of the area of interest. In one embodiment, the infrared radiation source and the imager are incorporated into a single unit.

Finally, at block 350, the imaging data acquired by the infrared camera is transmitted to a processor. In one embodiment, the processor can be coupled to the infrared camera, and the data is transmitted through the use of wires. In one embodiment, the processor is located external to the infrared camera. The data can be transmitted either through wired or wireless transmissions. The process ends at block 399.

Figure 4:
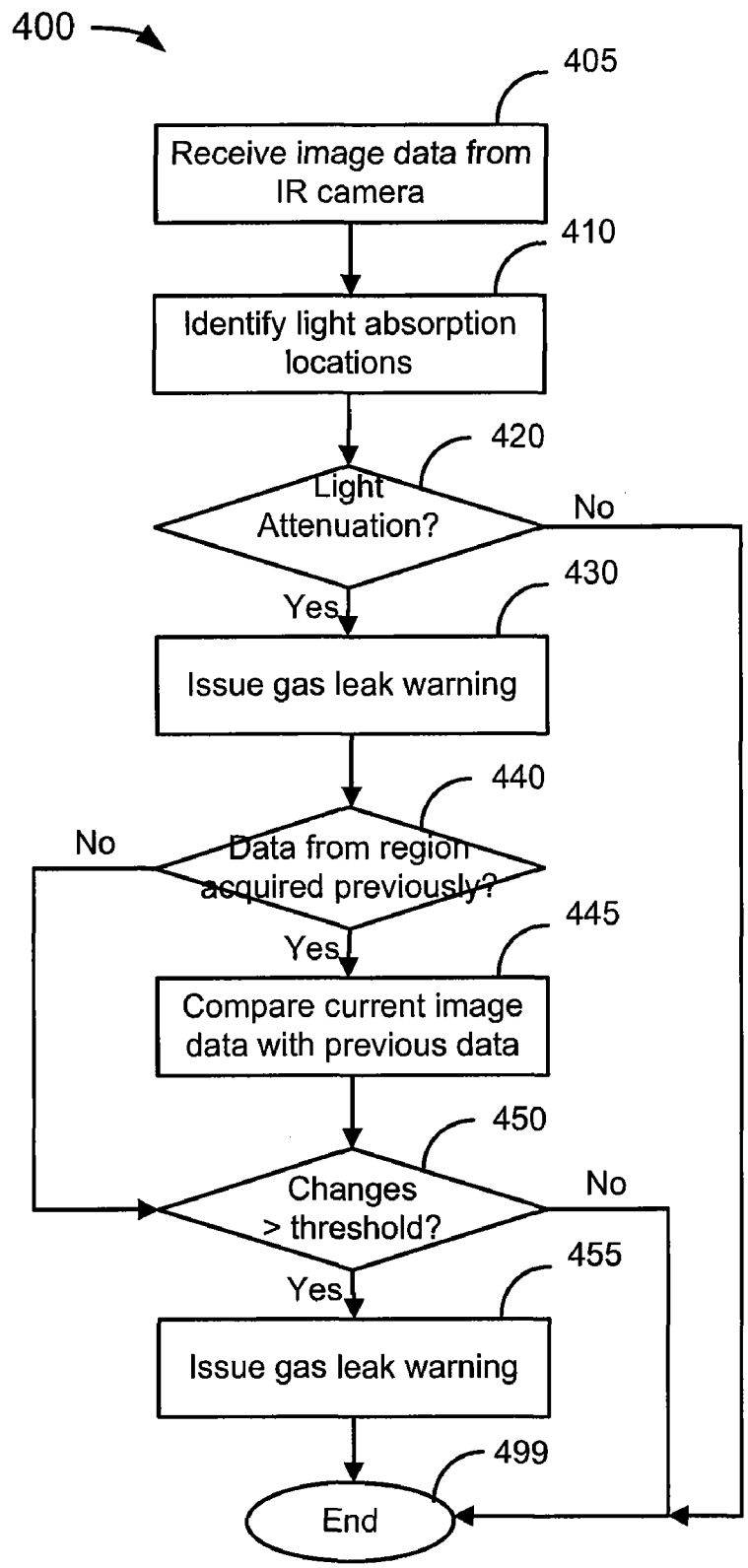
FIG. 4 depicts a flow diagram illustrating an exemplary process for detecting a gas leak from imaging data, according to an embodiment of the disclosure.

FIG. 4 depicts a flow diagram illustrating an exemplary process 400 for detecting a gas leak from imaging data, according to an embodiment of the disclosure.

At block 405, the image processor receives the image data from the infrared camera. Radiation absorption locations are identified at block 410. In one embodiment, the pixels of the image are normalized to the highest amplitude value of all of the image pixels. In one embodiment, false color images can be produced from the imaging data.

At decision block 420, the system determines whether there is any attenuation of the infrared radiation in the image. In one embodiment, multiple images can be taken of a particular area over a relatively short period of time, such as several minutes up to a few hours, to determine if there is a change in attenuation. A change in attenuation over time can indicate the presence of a leaking gas. If attenuation of infrared radiation is not detected (block 420—No), the process ends at block 499. If attenuation of infrared radiation is detected (block 420—Yes), at block 430 the system issues a gas leak warning. The warning may include sending leak locations or a processed image indicating leak locations in a transmission, such an email or text message, to a system administrator, sounding an alarm in the location of the leak to alert persons in the vicinity, and/or sending a leak locations to a maintenance and/or clean-up crew.

In one embodiment, the system may use an image processing algorithm to determine whether the attenuation of the infrared radiation at absorption locations is greater than a predetermined threshold. The threshold may be set at or close to zero for poisonous gases and may be set somewhat higher for other types of gases, depending on the risks and costs associated with identifying and fixing leaks.

At decision block 440, the system determines if the imaging data that was received from the infrared camera at block 405 was from a region that has been imaged previously. If the imaging data is not from a previously imaged location (block 440—No), the process continues to decision block 450, as described below. If the imaging data is from a previously imaged location (block 440—Yes), at block 445 the processor compares the current imaging data with the most recent previously imaged data to determine if there have been any long-term changes in radiation absorption, thus indicating that the magnitude of the gas leak has changed. In one embodiment, the current imaging data can be compared with a series of previously imaged data, if available, to determine the development progression of any gas leaks.

At decision block 450, the system determines if the changes in the imaging data are greater than a predetermined threshold. If there are no changes or if the changes are less than the threshold (block 450—No), the process ends at block 499. If the changes are greater in magnitude than the threshold (block—Yes), at block 455 the system issues a gas leak warning. The warning may be similar to the warnings detailed at block 430 above. The process ends at block 499.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this patent application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or sub-combinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. An apparatus for detecting presence of a gas, comprising:
   a source configured to generate a band of infrared radiation tunable over a range of wavelengths, wherein a gas to be detected has an absorption band within the range of wavelengths, and further wherein the source can be tuned to the absorption band of the gas to be detected;
   an infrared detecting element configured to receive infrared radiation reflected from an area to be checked for the presence of gas and generate an image from the reflected infrared radiation;
   a plurality of filters coupled to the infrared detecting element configured to filter the reflected infrared radiation received by the infrared detecting element, wherein one or a combination of at least some of the plurality of filters are selectable based upon the absorption band of the gas to be detected to attenuate wavelengths of radiation outside the absorption band.

2. The apparatus of claim 1, further comprising a processor to process the reflected infrared radiation to determine any locations where at least one of the plurality of gases is present or leaking.

3. The apparatus of claim 1, further comprising a reflector located behind the area, wherein the reflector reflects at least at wavelengths within one of the absorption bands of the plurality of gases, and further wherein the reflector is large enough to provide reflections of infrared radiation over the entire area.

4. The apparatus of claim 3 wherein the reflector comprises an aluminized material.

5. The apparatus of claim 1 wherein the infrared detecting element scans at least a portion of the area.

6. The apparatus of claim 1 wherein the band of infrared radiation is narrowband.

7. The apparatus of claim 1 wherein the plurality of filters comprises one or more optical filters selected from a group consisting of lowpass filters, highpass filters, and bandpass filters.

8. An apparatus for detecting gas leaks, comprising:
   means for generating infrared radiation for illuminating an area, wherein the infrared radiation is tunable over a range of wavelengths, wherein a plurality of gases to be detected have absorption bands within the range of wavelengths;
   means for imaging a reflected infrared radiation from at least a portion of the area;
   means for filtering the reflected infrared radiation by at least attenuating wavelengths of radiation outside an absorption band of the gas.

9. The apparatus of claim 8, further comprising a processor to process the reflected infrared radiation to determine locations of the gas or gas leaks.

10. A method of detecting a plurality of gases, comprising:
    providing a source that generates a band of infrared radiation tunable over a range of wavelengths, wherein the plurality of gases have absorption bands within the range of wavelengths, and further wherein the absorption bands of the gases are within atmospheric transmission windows;
    tuning the band of infrared radiation to a first absorption band of a first gas to be detected;
    directing the infrared radiation to illuminate an area;
    receiving and imaging at least a portion of the infrared radiation reflected from the area;
    filtering the received infrared radiation to at least attenuate wavelengths outside the first absorption band of the first gas;
    identifying one or more locations of the first gas by determining where the received infrared radiation is attenuated.

11. The method of claim 10, further comprising generating an alarm if the received infrared radiation in the absorption band is attenuated more than a first predetermined threshold at any location.

12. The method of claim 10, further comprising placing a reflector behind the area, wherein the reflector reflects at least at the wavelengths in the absorption band.

13. The method of claim 10, wherein receiving the infrared radiation comprises scanning an infrared imager over a region of the area.

14. The method of claim 10, further comprising gating the source to improve a signal to noise ratio.

15. The method of claim 10, wherein filtering the received infrared radiation comprises using one or more optical filters.

16. A system for detecting one or more gases, comprising:
    an infrared detecting element configured to receive infrared radiation reflected from an area and generate an image from the reflected infrared radiation;
    at least one optical filter configured to filter the reflected infrared radiation received by the infrared detecting element by at least attenuating wavelengths of radiation outside an absorption band of the gas;
    a reflector located behind the area, wherein the reflector reflects at least at wavelengths within the absorption band of the gas, and further wherein the reflector is large enough to provide reflections of infrared radiation over the entire area.

17. The system of claim 16, further comprising a source that generates the infrared radiation that reflects from the area.

18. The system of claim 16, wherein the reflector comprises an aluminized material.

19. The system of cliam 16, further comprising a processor to process the reflected infrared radiation to determine any locations where at least one of the one or more gases is present or leaking.

\* \* \* \* \*